Figure 1:
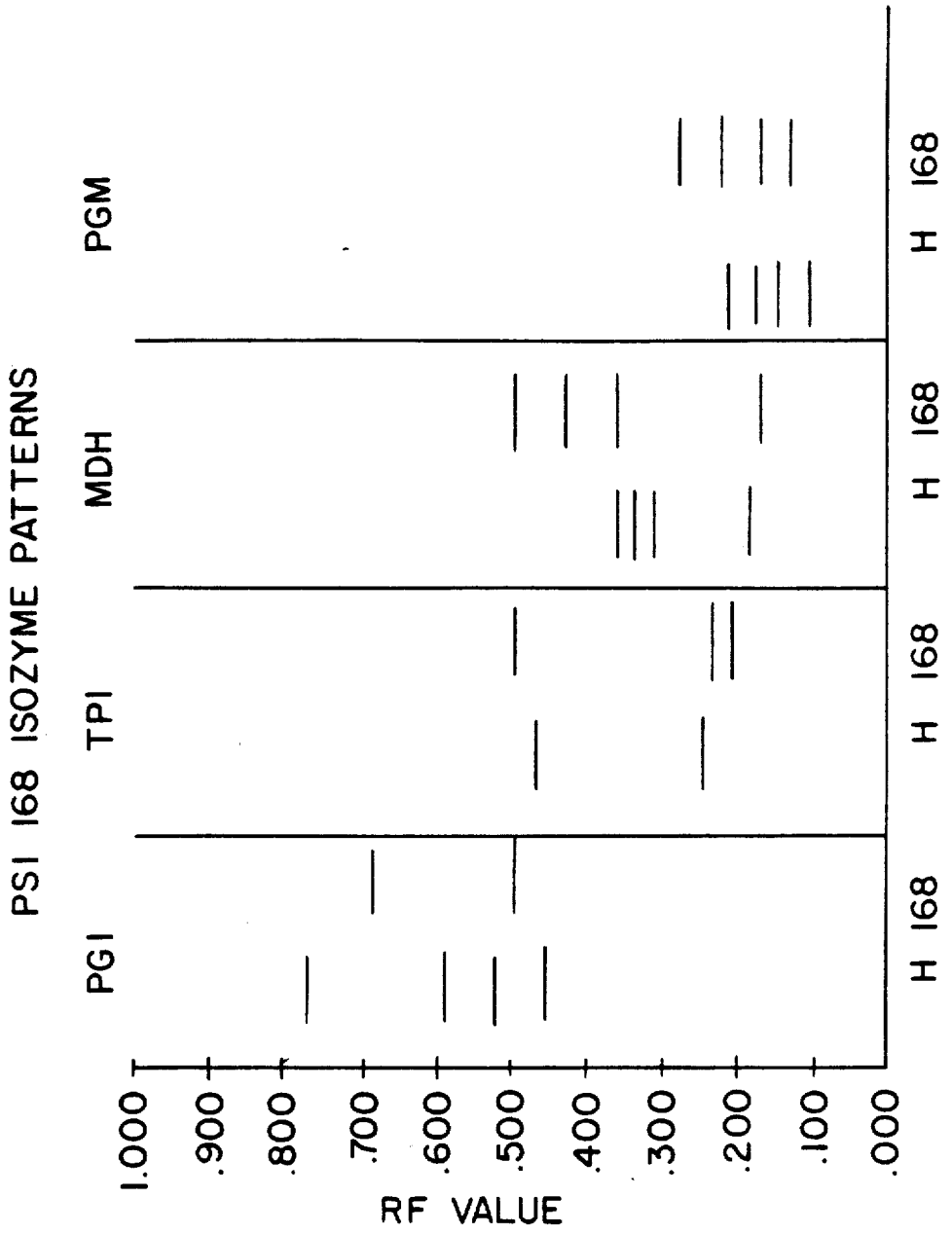

United States Patent [19]

Ackerman

[11] Patent Number: Plant 7,528

[45] Date of Patent: May 21, 1991

[54] RASPBERRY PLANT NAME PSI 168

[75] Inventor: Stephen M. Ackerman, Salinas, Calif.

[73] Assignee: Plant Sciences, Inc., Watsonville, Calif.

[21] Appl. No.: 398,431

[22] Filed: Aug. 25, 1989

[51] Int. Cl.[5] ..... A01H 5/00

[52] U.S. Cl. ..... Plt./46

[58] Field of Search ..... Plt./46

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A distinct red raspberry variety named PSI 168, characterized by everbearing fruit habit, high yields, early fruiting habit on second year floricanes, and many small and reduced thorns. Berry size averages 3.3 to 3.4 grams, from August through November.

4 Drawing Sheets

1

My invention relates to a new and distinct everbearing red raspberry variety named PSI 168, botanically known as *Rubus idaeus*. It was discovered by me as a chance seedling in a breeding plot established in 1987 on a ranch in Watsonville, Calif., provided by Well-Pict, Inc. of Watsonville.

A breeding program was initiated jointly by Plant Sciences, Inc., and Coast Cooling, Inc. with the goal of developing new and distinct raspberry varieties. In 1987, my new variety was selected, and extensively tested over the next year.

On Dec. 30, 1987, 15 to 20 dormat sucker cans of the variety were dug from the 1988 seedling field located on the Flats Ranch, Watsonville, Calif. All canes were hand dug as dormant root stock, cleaned, bagged and boxed. The canes were stored at a local cold storage facility at 28° F. until planting. These canes were planted on Jan. 26, 1988, in 15 to 20 linear feet of bed in the 1988 selection field, also located on the Flats Ranch.

On Nov. 30, 1988, 100 dormant sucker canes of the variety were dug from the 1988 selection field located on the Flats Ranch, for further propagation. The following lists the planting dates, number of plants propagated and location of each planting.

| Planting Date | No. Plants | Location/Watsonville, CA |
|---|---|---|
| 12-30-88 | 40* | Peckham Ranch |
| 1-19-89 | 15** | Flats Ranch |
| 1-19-89 | 6* | Nakano Ranch |
| 1-25-89 | 20* | Peckham Ranch |
| 4-30/5-2-89 | 2,000-3,000*** | Flats Ranch |

*Planted as dormant bare root stock for field evaluations.

**Planted as dormant bare root stock for field evaluations in the 1989 advanced selection field.

***Planted or commerical nursery stock as greenhouse matured shoot tips propagated from 8-10 lbs. of roots.

The variety has been reproduced through asexually propagated sucker plants from selection fields in Watsonville, Calif. These daughter plants were then relocated for further testing on local grower fields associated with Well-Pict, Inc. in the Watsonville/Salinas area. Through these further tests and subsequent generations, the characteristics of the novel variety remained fixed and true to type.

The following features are particularly outstanding in my new variety:

1. Everbearing fruiting habit, fruits on first year primocanes.

2

2. High yields, producing about 65 percent of its overall spring production in June.

3. Early fruiting habits on second year floricanes, typically 1-2 weeks earlier than Willamette, and one week later than PSI 114 or PSI 127.

4. Exceptional vigor, producing twice as many suckers as Heritage.

5. Reduced thorns, about 25 percent smaller than PSI 114, PSI 127 or PSI 79, and twice as small as Heritage.

The accompanying photographs show typical specimens of my new red raspberry variety at various stages of development.

Photograph 1 shows a section of a typical primocane with its many small and reduced thorns, foliage, fruit, flowers, and a typical fruiting terminal.

Photograph 2 shows the developmental stages of a berry from flower to maturity, and also the purple coloration of a typical primocane.

Photograph 3 shows a typical fruiting terminal, with the exposure of the fruit that makes this variety very easy to pick. It also shows the irregular shapes of the drupelets leading to irregularity of fruit shape.

FIG. 1 illustrates the electrophoresis patterns unique to this variety, as explained in detail below.

Production on first year primocanes begins approximately on August 1, yielding 10 percent of its total production in August, 60 percent in September, 20 percent in October, and 10 percent in November, peaking during the middle of September. Berry size averages 3.3 to 3.4 grams from August through November, (about 25 percent larger than Heritage).

Spring production on second year floricanes begins approximately on May 10, yielding 15 percent of its total production in May, 60 percent in June and 25 percent in July, peaking during the middle of June. Berry size averages 2.3 to 2.5 grams from May through July (about 20 percent smaller than Willamette).

The spring crop typically comprises 65 percent of the total production, with th fall crop comprising 35 percent. The spring crop precedes Willamette by approximately one week, with yields throughout the year exceeding those of both Heritage and Willamette.

The following is a detailed description of my new variety, based upon observations taken in Watsonville, Calif. Color terminology is in accordance with the Munsell Book of Colors, Munsell Color, Baltimore, Md. (1976).

Parentage: An open pollinated seedling of unknown parentage.

Fruit: Conditions when described; late (Oct. 27, 1988).

*Color.*—Red, color 7.5R 3/8 to 7.5R 3/10.

*Size.*—Averages 18.2 mm long × 18.3 mm wide (2.5 grams).

*Shape.*—Ovate, tapering to a rounded tip.

*Cavity.*—Funnel shaped, size averages 14.3 mm deep × 8.0 mm wide.

*Receptable.*—Cone shaped, size averages 12.5 mm long × 9.0 mm wide at the base, tapering to a sharp point. Color 10Y 9/4 to 10Y 8.5/4.

*Drupelets.*—Small, irregular in shape, average 75–85 per berry, and 16–17 around the outer rim.

*Seeds.*—Small, average 2.8 mm, long × 1.6 mm wide × 1.0 mm thick. Average weight, 1.3 milligrams per seed. Surface rugose. Color tan, 10YR 8/4 to 10YR 7/4.

*Sepals.*—Acuminate, number — 5, color 5GY 6/6 to 5GY 7/6.

*Petals.*—Obovate, number — 5.

*Quality.*—Very good fresh. Holds uniformity in color and appearance through cold storage and shipping. Fruit is well exposed and easy to pick. Detaches easily from receptacle.

Plant: Data are an average of two evaluations, made on Sept. 23, 1988 and Oct. 12, 1988.

*Growth.*—Vigorous.

*Crown.*—Branched.

*Leaves.*—All samples were taken from a fully mature trifoliate, 10 to 12 trifoliates from the terminal bud. Leaves are moderately corrugated. Foliage is nearly always three foliage. Occasionally, the central leaflet will develop points to true independent leaflets, thus, creating a four foliate. Central leaflet: Size — averages 11.6 cm long × 10.6 cm wide; Shape — cordate, tapering to an acuminate point. Color — upper surface 7.5GY 4/4 to 7.5GY 3/4, lower surface 5GY 7/2 to 5GY 6/2. Lateral leaflet: Size — averages 9.3 cm long × 7.0 cm wide. Shape — ovate tapering to an acuminate point. Petiole averages 4.1 to 4.3 cm long and 2.7 to 2.9 mm in diameter.

*Canes.*—Moderately tall, average from 1.3 to 1.5 meters tall with an average basal diameter of 1.3 to 1.4 cm. Color, evaluated on Feb. 10, 1989, is light-medium brown, 7.5YR 4/4 to 7.5YR 6/4. Internode length averages 3.8 to 4.0 cm at mid cane. Produces on the upper 30 percent of its cane an average of 9 to 10 fruiting laterals, with an average length of up to 35–40 cm. Fruit is borne in raceme clusters, averaging 6 to 7 berries per terminal prior to the first trifoliate.

*Suckers.*—Produces an average of 7–9 suckers per linear foot of bed planted in a single row and spaced 12 inches apart. Average basal diameter — 0.6 to 0.8 cm. Glaborous, with many small soft prickles, heavy at the base, averaging 30 per cm of cane by 1.4 mm long, to 12 per cm at the tip by 0.9 mm long. Internode length — averages 3.9 to 4.1 cm at mid cane. Color is light green, 5 GY 6/6 to 5GY 7/6. With age and exposure to the sun, suckers tends toward a purple coloration, 10RP 3/6 to 10RP 5.6.

My new variety may not be resistant to any known diseases and insects. It is known to be susceptible to powdery mildew and rust. This new variety may vary slightly in description, depending upon weather, soil, location, and evaluation dates.

Studies of protein polymorphism in Rubus by the starch gel electrophoresis method were carried out to characterize this newly developed variety and further distinguish it from other varieties.

Isozymes were extracted from young leaves and characterized using starch gel electrophoresis techniques. The following isozymes were characterized: malate dehydrogenase (MDH: EC 1.1.1.37); triose phosphate isomerase (TPI: EC 5.3.1.1); phosphoglucoisomerase (PGI: EC 5.3.1.9) and phosphoglucomutase (PGM: EC 2.7.5.1).

The plant material used in the characterization was both field and green-house grown in Watsonville, Calif. Newly matured leaves (1 g fresh weight) from the growing tips of canes were used. Samples were held at 4–8C and analyzed within 24 hours of collection.

The tris extraction buffer (pH 8.0) was as follows: 0.05M tris base, 0.007M citric acid (monohydrate), 0.1% cysteine hydrochloride, 0.1% ascorbic acid (Na salt or free acid), 1.0% polyethylene glycol, and 80 ul/l 2-mercaptoethanol. Samples were extracted in 10–12 ml cold buffer by homogenizing at 17,000 rpm.

Gel and electrode buffers for the four enzyme systems analyzed are given in Table 1. Electrophoresis specifications for the enzyme systems are given in Table 2.

The starch gel used for electrophoresis is prepared and held overnight at 20±5C prior to use. To make the gel, potato starch (30 g) is dissolved in 80 ml of cold gel buffer (System A: gel buffer 50 ml/electrode buffer 30 ml) is added to the starch solution in a vacuum flask (1.0 l). Boiling gel buffer (220 ml). The starch is completely dissolved by vigorously swirling the solution in the vacuum flask, and then vacuumed for 15 to 30 seconds. Gel solution is immediately poured onto a 20.5 × 22.0 cm plexiglass gel plate and covered until use.

Samples are inoculated onto paper wicks and placed in a cooled gel (4C); covered with Saran and electrophoresed for 20 minutes. The wicks are removed and the system is run until the dye front travels approximately 5–8 cm.

Following electrophoresis, the gel is sliced into four equal slices and stained for each enzyme system. Banding patterns are interpreted as they develop and gel slices are fixed in 50% glycerol.

TABLE 1

| SYSTEM | pH | GEL BUFFER | G/L | ELECTRODE BUFFER | G/L | pH |
|---|---|---|---|---|---|---|
| A | 8.3 | Tris Base | 65 | Lithium Hydroxide | 1.2 | 8.3 |
| | | Citric Acid (Monoh) | 1.5 | Boric Acid | 12.0 | |
| B | 7.0 | DL-Histidine HCL (Monohydrate) | 1.2 | Tris Base | 16.5 | 7.0 |
| | | | | Citric Acid (Monohyd.) | 9.0 | |
| C | 7.8 | Tris Ultra Pure | 1.09 | Tris Ultra Pure | 16.35 | 7.8 |
| | | Citric Acid | 0.63 | Citric Acid | 9.03 | |
| | | $Na_2EDTA$ | 0.45 | $Na_2EDTA$ | 0.45 | |

TABLE 2

RUBUS ELECTROPHORESIS SPECIFICATIONS

| SYSTEM | ENZYME | pH | CURRENT | GEL SLICE # |
|---|---|---|---|---|
| A | PGI | 8.3 | 275V | 2 |
| A | LAP | 8.3 | 275V | 4 |
| B | MDH | 7.0 | 150V | 2 |

TABLE 2-continued

| RUBUS ELECTROPHORESIS SPECIFICATIONS | | | | |
|---|---|---|---|---|
| SYSTEM | ENZYME | pH | CURRENT | GEL SLICE # |
| B | PGM | 7.0 | 150V | 3 |
| C | TPI | 7.8 | 50mA | 2 |

The isozyme banding patterns for the four enzyme systems compared to those of Heritage are given in FIG. 1. The RF value is the ratio between the distance (cm) traveled by the band to the distance traveled by the dye front (cm).

What is claimed is:

1. A new and distinct variety of red raspberry plant named PSI 168, as herein described and illustrated.

* * * * *

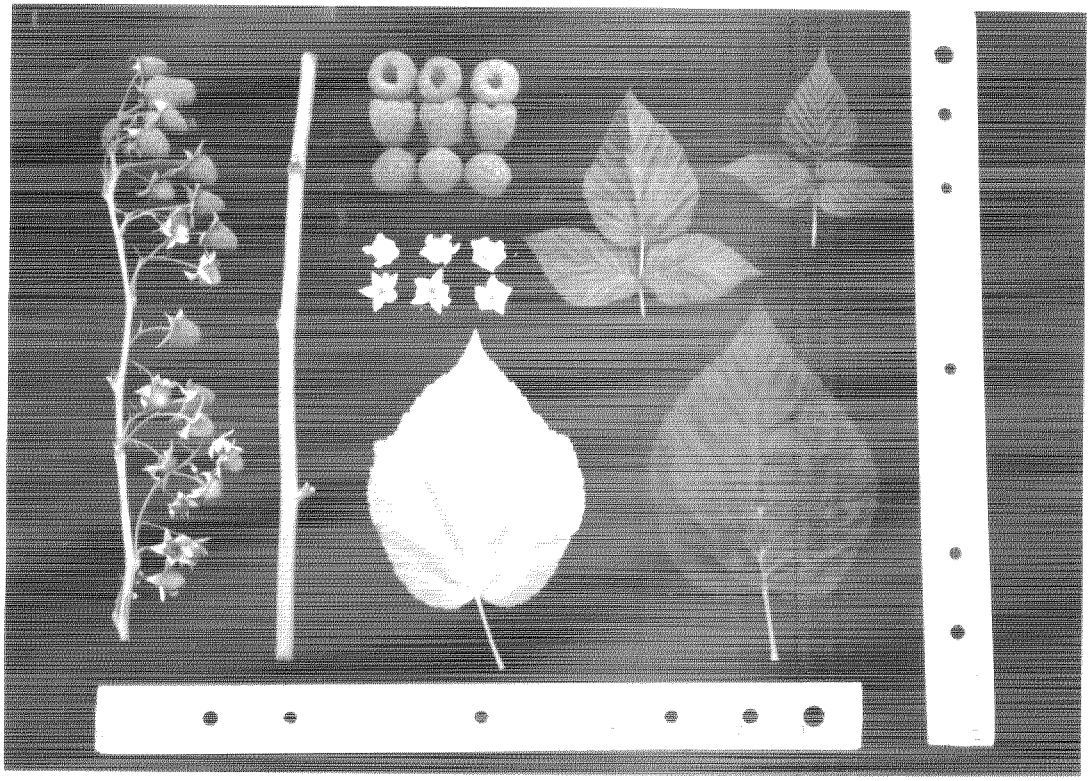

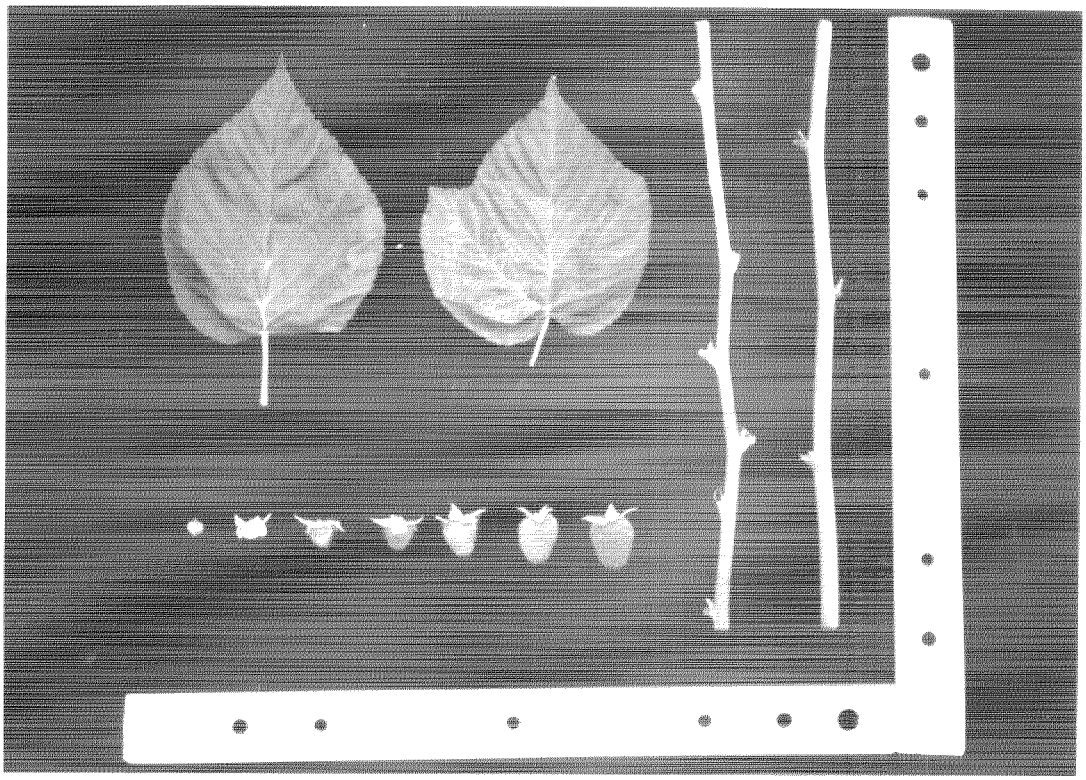

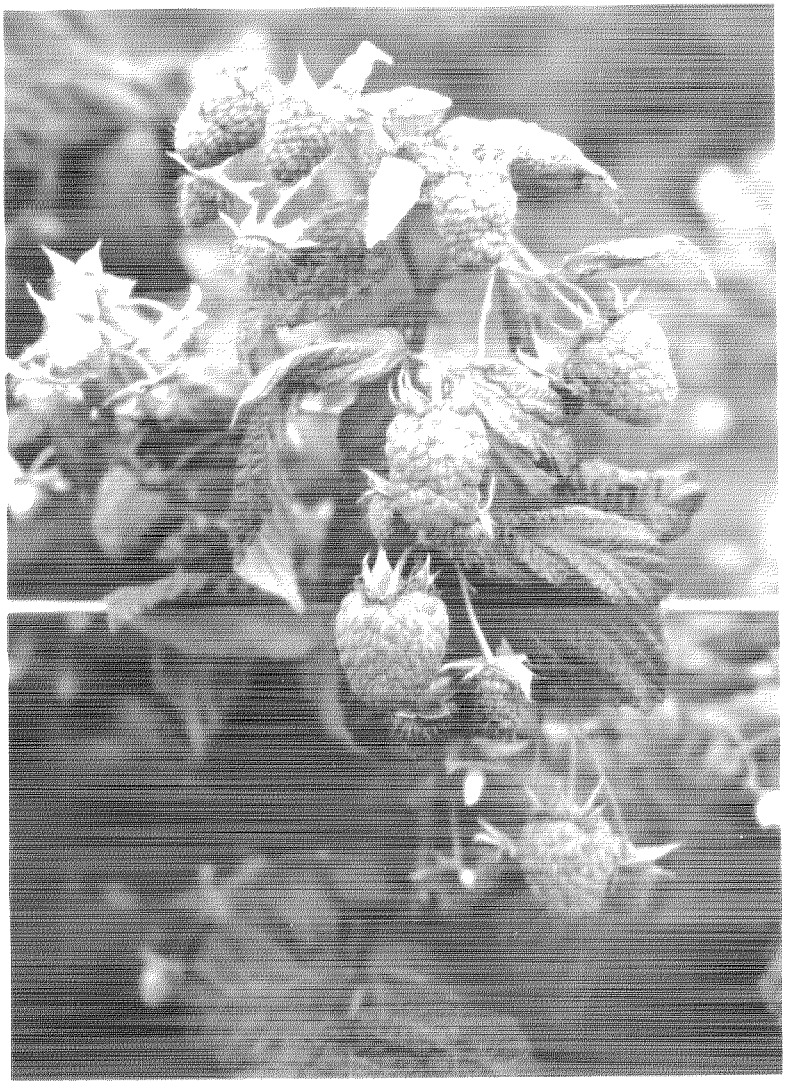

UNITED STATES PATENT AND TRADEMARK OFFICE

CERTIFICATE OF CORRECTION

PATENT NO. : PP7528

DATED : May 21, 1991

INVENTOR(S) : Stephen Ackerman

It is certified that error appears in the above—identified patent and that said Letters Patent is hereby corrected as shown below:

Column 1, line 12, delete "cans" and insert --canes--.

Column 2, line 40, delete "th" and insert --the--.

Column 3, line 33, delete "foliage" and insert --foliate--.

Signed and Sealed this

Thirtieth Day of March, 1993

*Attest:*

STEPHEN G. KUNIN

*Attesting Officer*

*Acting Commissioner of Patents and Trademarks*